United States Patent
DiPalma

(10) Patent No.: US 6,436,328 B1
(45) Date of Patent: Aug. 20, 2002

(54) METHOD FOR FORMING AN ABSORBENT STRUCTURE

(75) Inventor: Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/396,717

(22) Filed: Sep. 15, 1999

(51) Int. Cl.[7] .......................... A61F 13/32; B29C 70/68; B27N 5/02
(52) U.S. Cl. .................. 264/254; 264/238; 264/258; 264/294; 264/324; 156/185; 156/190; 156/191; 428/37; 604/378
(58) Field of Search .................. 264/258, 294, 264/279.1, 254, 238, 324; 604/367, 368, 369, 370, 378, 385.01, 385.101, 385.17, 385.18; 428/37; 156/184, 185, 190, 191

(56) References Cited

U.S. PATENT DOCUMENTS

| | | | |
|---|---|---|---|
| 3,358,354 A | * 12/1967 | Voss et al. .................. 29/419.1 |
| 3,581,744 A | * 6/1971 | Voss .............................. 604/14 |
| 3,668,054 A | 6/1972 | Stumpf | |
| 3,724,463 A | * 4/1973 | Vail ................................ 604/1 |
| 3,818,912 A | * 6/1974 | Etz .............................. 604/358 |
| 3,999,549 A | * 12/1976 | Poncy et al. .................. 604/15 |
| 4,078,123 A | * 3/1978 | Costenoble ................. 429/141 |
| 4,100,324 A | 7/1978 | Anderson et al. | |
| 4,340,058 A | 7/1982 | Pierce et al. | |
| 4,351,339 A | * 9/1982 | Sneider ......................... 604/11 |
| 4,374,522 A | * 2/1983 | Olevsky ..................... 604/374 |
| 4,467,012 A | 8/1984 | Pedersen et al. | |
| 4,573,990 A | 3/1986 | Ohsaki | |
| 4,610,659 A | * 9/1986 | Friese ........................... 604/11 |
| 4,616,644 A | 10/1986 | Saferstein et al. | |
| 4,622,030 A | 11/1986 | Sheldon et al. | |
| 4,627,848 A | 12/1986 | Lassen et al. ............... 604/370 |

(List continued on next page.)

FOREIGN PATENT DOCUMENTS

| | | |
|---|---|---|
| EP | 339461 | 11/1989 |
| EP | 607 985 | 7/1994 |
| EP | 868 894 | 10/1998 |
| WO | 95/24174 | 9/1995 |
| WO | 96/34589 | 11/1996 |
| WO | 99/32165 | 7/1999 |

*Primary Examiner*—Jan H. Silbaugh
*Assistant Examiner*—Stefan Staicovici
(74) *Attorney, Agent, or Firm*—Pauley Peterson Kinne & Erickson

(57) ABSTRACT

A method for forming an absorbent article having an absorbent pad assembly with an outer fluid-contacting surface including discrete portions of different absorbency is provided. At least first and second absorbent pad materials are helically wound adjacently about a shaft member whereby at least a portion of each of the first and second absorbent pad materials includes an outer surface exposed portion.

40 Claims, 7 Drawing Sheets

U.S. PATENT DOCUMENTS

| | | | |
|---|---|---|---|
| RE32,649 E | | 4/1988 | Brandt et al. |
| 4,798,603 A | | 1/1989 | Meyer et al. |
| 4,908,026 A | | 3/1990 | Sukiennik et al. |
| 5,019,061 A | * | 5/1991 | Hoden et al. ............... 604/358 |
| 5,104,396 A | | 4/1992 | Oatley et al. |
| 5,175,046 A | | 12/1992 | Nguyen |
| 5,248,309 A | | 9/1993 | Serbiak et al. |
| 5,336,552 A | | 8/1994 | Strack et al. |
| 5,346,287 A | * | 9/1994 | Burrow et al. ................ 300/21 |
| 5,360,504 A | | 11/1994 | Fell et al. |
| 5,364,382 A | | 11/1994 | Latimer et al. |
| 5,366,450 A | | 11/1994 | DeGroot |
| 5,383,870 A | | 1/1995 | Takai et al. |
| 5,387,209 A | | 2/1995 | Yamamoto et al. |
| 5,401,267 A | | 3/1995 | Couture-Dorschner et al. |
| 5,490,846 A | | 2/1996 | Ellis et al. |
| 5,505,720 A | | 4/1996 | Walters et al. |
| 5,506,277 A | | 4/1996 | Griesbach, III |
| 5,554,108 A | * | 9/1996 | Browning et al. ............. 604/15 |
| 5,609,586 A | * | 3/1997 | Zadini et al. ................ 604/358 |
| 5,643,240 A | | 7/1997 | Jackson et al. |
| 5,647,862 A | | 7/1997 | Osborn III et al. |
| 5,649,916 A | | 7/1997 | DiPalma et al. |
| 5,656,361 A | | 8/1997 | Vogt et al. |
| 5,688,257 A | * | 11/1997 | Olsen .......................... 604/363 |
| 5,785,697 A | | 7/1998 | Trombetta et al. |
| 5,843,063 A | | 12/1998 | Anderson et al. |
| 5,853,402 A | | 12/1998 | Faulks et al. |
| 5,879,343 A | | 3/1999 | Dodge, II et al. |
| 5,893,956 A | * | 4/1999 | Perry, Jr. et al. ............. 156/167 |
| 6,059,763 A | * | 5/2000 | Brown ................... 604/385.17 |
| 6,177,608 B1 | * | 1/2001 | Weinstrauch ............... 604/380 |

* cited by examiner

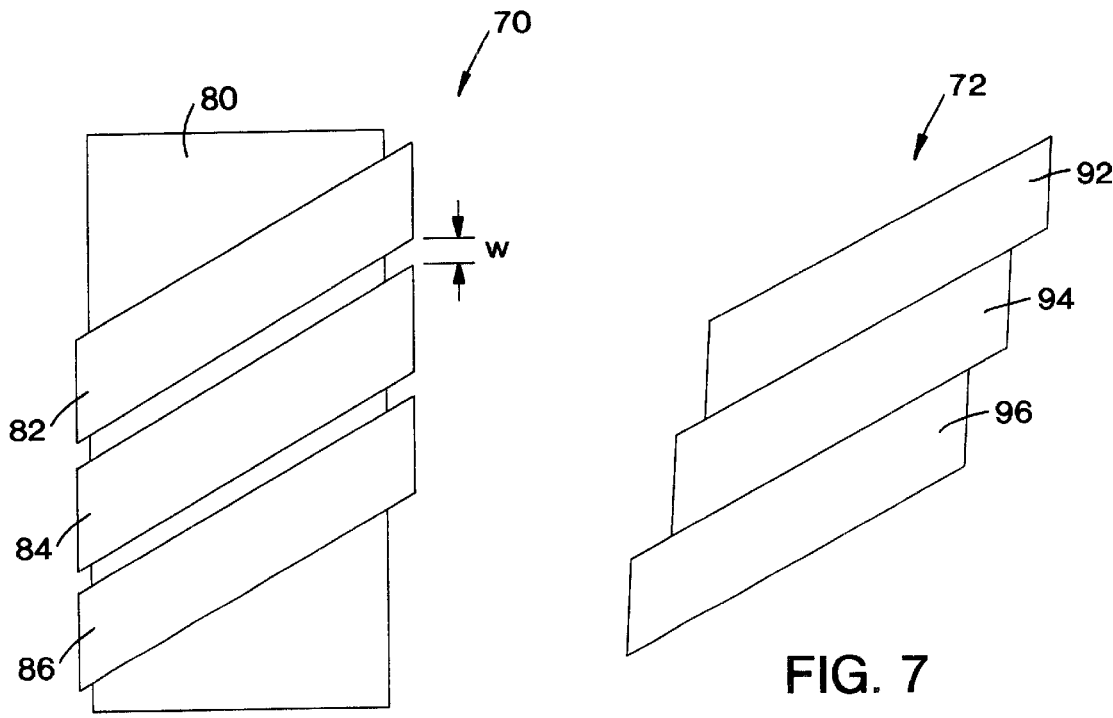
FIG. 6
FIG. 7
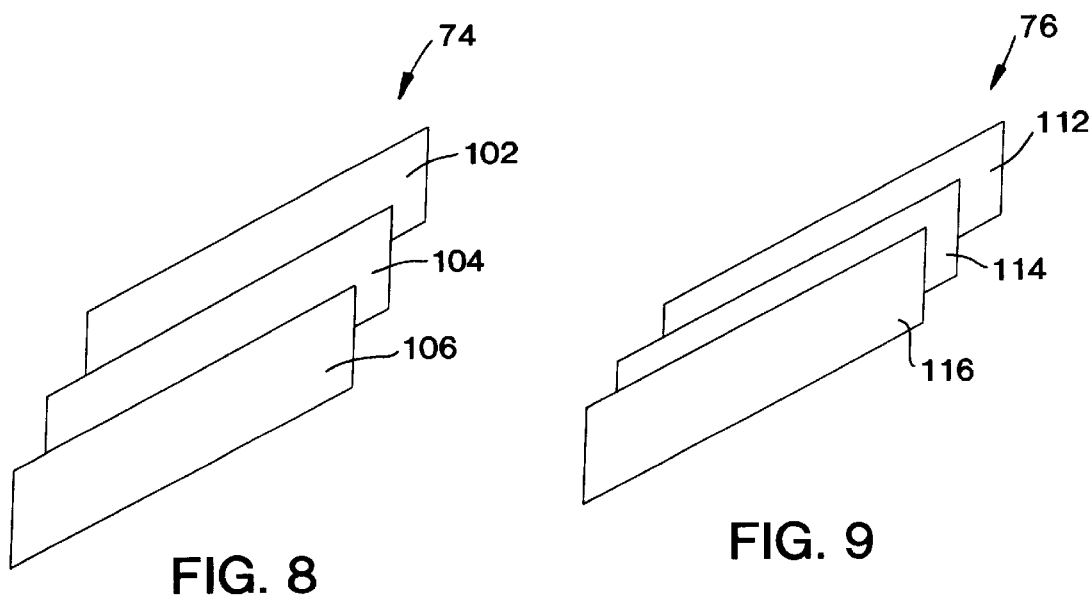
FIG. 8
FIG. 9

METHOD FOR FORMING AN ABSORBENT STRUCTURE

FIELD OF THE INVENTION

This invention relates generally to absorbent articles for absorbing body fluids and exudates. More particularly, the present invention relates to a method for forming an absorbent structure having improved leak prevention and/or fluid flow control.

BACKGROUND OF THE INVENTION

A wide variety of types of structures are known in the art for use in or as absorbent articles, particularly disposable absorbent articles, used to collect various body fluids and exudates. Commercial absorbent articles include diapers, adult incontinence products, sanitary napkins and bandages. Disposable products of these types generally comprise components for receiving, absorbing and retaining fluids. Typically, the components of such articles include a liquid permeable topsheet, an absorbent core and a liquid impermeable backsheet.

The components of typical absorbent articles are commonly plied or arranged in a horizontal fashion with a major planar surface facing the fluid intake area, e.g., the body of the wearer. In such absorbent articles, the nature or make-up of the fluid communicating therethrough can and typically will change as such fluid traverses though the horizontal ply or plies. Thus, such absorbent articles may experience undesirable horizontal dependency between components. Further, the fibers which customarily make-up the absorbent core are often orientated randomly with fibers within a mat in a lateral neighboring arrangement such that the fluid intake typically wicks in a radial fashion or pattern.

One of the main objectives in the development of absorbent articles is to increase, improve or maximize utilization of the absorbent capacity of the article. In general, products of the type described above typically distribute fluids deposited on the topsheet in a circular pattern. Since such structures generally have a length that exceeds their width, such liquid distribution may undesirably result in the fluids, e.g., exudates, reaching the longitudinal side edges of the absorbent article prior to the desirable utilization of the absorbent capacity at the end regions of the absorbent article. As will be appreciated, such occurrence may undesirably increase the possibility or likelihood of leakage from the sides of the article despite the availability of unutilized or underutilized absorbent capacity in the end regions of the absorbent article.

Moreover, such absorbent articles can and may be subjected to a wide range of conditions and applications such as due to factors inherent or related to the environment in which the article is utilized. Thus, the fluids which may need to be absorbed thereby may vary in properties or parameters such as including flow rate as well as form, phase or composition. For example, exudates may be multiphasic and heterogeneous, such as in the case of menses which may include red blood cells, mucin, plasma and tissue debris, for example.

Sanitary napkins (also referred to as catamenial pads), feminine pads, overnight pads, panty liners and panty shields are designed to be worn by a female to absorb menses and other body fluids discharged before, during and after a menstrual period. Sanitary napkins are external devices which are designed to be aligned approximate the pudendum region of a human body and are generally held in position by being adhesively or mechanically attached to an undergarment. Sanitary napkins also typically differ from panty liners and panty shields in several notable ways. Sanitary napkins are generally larger in size and have a more defined 3-dimensional configuration, are thicker in caliper and have a greater fluid capacity than panty liners or panty shields.

In view of the desire to provide increased comfort to the wearer and to minimize the appearance of the presence of such absorbent articles there is an ongoing demand and need for smaller or less bulky absorbent articles. Thus, there is a need and a demand for improved absorbent pad assemblies and absorbent articles such as may result in more complete utilization of the absorbent capacity thereof and such as may more effectively and efficiently respond to the possibly wide range of operating and performance conditions to which such assemblies and articles can be exposed.

In addition, there is a need and a demand absorbent structures which, in association with the absorbency of particular body fluids, more readily permit or provide the simultaneous or near simultaneous exposure of such fluids to absorbent materials of different selected absorbency. Further, there is a need and a demand for an improved technique or method of forming such absorbent structures. In particular, there is a need and a demand for such a formation technique or method which is either or both simpler or more effective than otherwise known or available.

SUMMARY OF THE INVENTION

A general object of the invention is to provide an improved method of forming an absorbent pad assembly, absorbent article or other selected absorbent structure or product.

A more specific objective of the invention is to overcome one or more of the problems described above.

The general object of the invention can be attained, at least in part and in accordance with one embodiment of the invention via a specific method for forming an absorbent article having an absorbent pad assembly with an outer fluid-contacting surface including discrete portions of different absorbency. A method, in accordance with one specific embodiment of the invention, involves helically winding at least first and second absorbent pad materials adjacently about a shaft member whereby at least a portion of each of the first and second absorbent pad materials includes an outer surface exposed portion.

The prior art generally fails to provide absorbent pad assemblies and absorbent articles which make as complete or full, as may be desired, utilization of the absorbent capacity of the respective absorbent structure. The prior art also generally fails to provide absorbent pad assemblies and absorbent articles which can respond either or both as effectively and as efficiently as may be desired to the possibly wide range of operating and performance conditions to which such assemblies and articles can be exposed. In particular, the prior art generally fails to provide such absorbent pad assemblies and absorbent articles of as simple as desired construction, fabrication and/or formation.

The invention further comprehends a method for forming an absorbent article having an absorbent pad assembly with a longitudinal axis and an outer fluid-contacting surface including discrete portions of different absorbency. In accordance with one embodiment of the invention, such a method includes helically winding at least first, second and third absorbent pad materials adjacently about a shaft member whereby at least a portion of each of the first, second and third absorbent pad materials includes an outer surface exposed portion. The absorbent pad assembly is then flattened along the longitudinal axis thereof. An absorbent core including the flattened absorbent pad assembly is then placed between a backsheet and a topsheet so as to form the absorbent article.

In accordance with another aspect of the invention, the invention comprehends a specific absorbent pad assembly. An absorbent pad assembly, in accordance with one preferred embodiment, has a longitudinal axis and includes a first absorbent pad material having a first preselected absorbency and a second absorbent pad material having a second preselected absorbency, where the first and preselected absorbencies are different. At least one section of the first absorbent pad material and at least one section of the second absorbent pad material are adjacently disposed relative to each other and the at least one section of the first absorbent pad material and the at least one section of the second absorbent pad material each have an edge surface angularly orientated relative to the longitudinal axis.

The invention further comprehends a specific absorbent article. An absorbent article, in accordance with one preferred embodiment of the invention, has a longitudinal axis and includes an absorbent pad assembly which forms an outer fluid-contacting surface. The absorbent pad assembly includes first, second and third absorbent pad materials each having a respective preselected absorbency with the preselected absorbency of the second absorbent pad material being different than the preselected absorbency of the first absorbent pad material and the preselected absorbency of the third absorbent pad material being different than the preselected absorbency of the second absorbent pad material. At least one section of the first absorbent pad material and at least one section of the second absorbent pad material are adjacently disposed relative to each other and the at least one section of the first absorbent pad material and the at least one section of the second absorbent pad material each have an edge surface angularly orientated relative to the longitudinal axis. Also, the at least one section of the second absorbent pad material and at least one section of the third absorbent pad material are adjacently disposed relative to each other and angularly orientated relative to the longitudinal axis.

As used herein, references to "absorbent article(s)" are to be understood to refer to products such as diapers, sanitary napkins, training pants, incontinent garments, overnight pads, panty liners, under arm shields and the like, which are used to absorb body fluids and exudates, such as urine, menses, blood, perspiration and other excrements discharged by the body.

Other objects and advantages will be apparent to those skilled in the art from the following detailed description taken in conjunction with the appended claims and drawings.

BRIEF DESCRIPTION OF THE DRAWINGS

FIGS. 6–9 are simplified side view schematics illustrating the positioning of sections of different absorbent materials in accordance with alternative embodiments of the invention.

DETAILED DESCRIPTION OF THE PRESENTLY PREFERRED EMBODIMENTS

The present invention, as is described in more detail below, provides an improved absorbent pad assembly and absorbent article as well as a method of forming such absorbent products.

Figure 1:
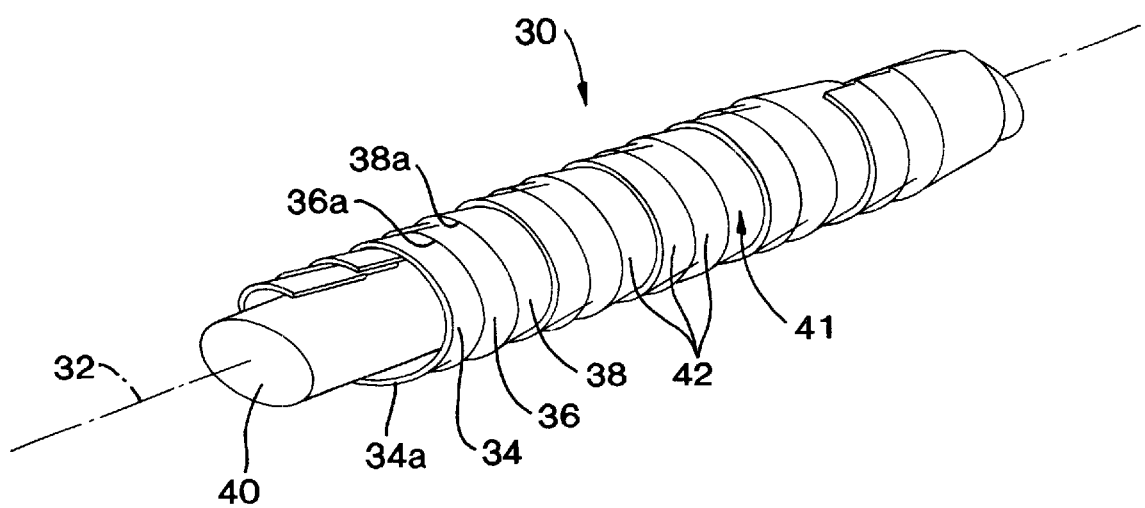
FIG. 1 is a simplified fragmentary perspective view of an absorbent pad assembly, in accordance with one preferred embodiment of the invention, with an associated mandrel.

Referring initially to FIG. 1, there is illustrated an absorbent pad assembly, generally designated by the reference numeral 30, in accordance with one embodiment of the invention and having a longitudinal axis designated by the reference numeral 32. As will be appreciated by those skilled in the art, such absorbent pad assemblies in accordance with the invention and as described in greater detail below, have particular utility in or as part of absorbent articles such as are generally capable of absorbing body fluid. Absorbent articles in accordance with the invention can take the form of diapers, training pants, sanitary napkins, panty liners, overnight pads, incontinence garments, underarm shields or other types of absorbent products capable of absorbing one or more bodily fluid such as urine, menses, blood, perspiration, excrement or the like. As will be appreciated, such absorbent articles will typically be disposable in nature.

The invention is perceived to have particular initial utility in or as a part of feminine care products such as in the form of sanitary napkins and the like. Thus, particular mention of such uses is made below. However, it is to be understood that the broader practice of the invention is not necessarily so limited and that the invention can, if desired be practiced in or in association with other types or forms of absorbent articles, such as identified above.

The absorbent pad assembly 30 is generally composed of adjacent windings of three webs or plies of absorbent pad material, individually designated 34, 36 and 38, wrapped about a generally cylindrical mandrel or shaft 40. While absorbent pad material webs used in the practice of the invention desirably are, as shown, each in continuous form such as to simplify manufacture and assembly, the broader practice of the invention is not necessarily so limited. For example, if desired, discontinuous sections of similar absorbent pad materials can, if desired, be used.

Each of the absorbent pad material webs 34, 36 and 38, respectively, includes an edge surface, individually designated 34a, 36a, and 38a, respectively. As shown, each absorbent pad material web 34, 36, and 38 is wound about the longitudinal axis 32, such as about the mandrel 40, such that each edge surface 34a, 36a and 38a, respectively, is angularly orientated relative to the longitudinal axis 32. Thus, it is to be appreciated, that absorbent pad assemblies in accordance with the invention do not constitute the mere layering of selected absorbent pad materials or absorbent pad material webs.

Further, as shown in FIG. 1, the outer surface 41 of the absorbent pad assembly 30 is generally composed of sections 42 of the absorbent pad material webs 34, 36 and 38, respectively. In accordance with one preferred embodiment of the invention, such outer surface 41 is, as shown, generally composed of sections 42 of each of the absorbent pad material webs 34, 36 and 38, respectively. As will be appreciated, such an absorbent pad assembly thus can serve to provide an outer surface such as composed of various specifically selected materials and such as may provide improved performance characteristics in particular product applications.

Suitable absorbent pad materials for particular uses, such as in feminine care products such as sanitary napkins and the like, are well known in the art. While particular absorbent pad materials for use in such absorbent articles are discussed below, in general each of the absorbent pad material webs 34, 36 and 38 preferably will have a preselected absorbency consistent with the intended use or utilization of the absorbent pad assembly 30.

Each of the absorbent pad material webs 34, 36 and 38 can be made of a material which is the same or different from the material of another of the webs of the assembly, as may be desired. In practice, however, in order to generally more completely realize the possible benefits attendant the practice of the invention, it is generally desirable that adjacent absorbent pad material webs differ in absorbency.

Further, while in its simplest form, the invention can be practiced using only two absorbent pad material webs, in accordance with certain preferred embodiments, absorbent pad assemblies are composed of three or more absorbent pad materials. For example, the inclusion of additional absorbent pad materials may permit an even greater amount of product design specificity to the assembly. As a result, products may be more specifically tailored to provide particular performance characteristics or qualities, as may be desired in certain applications.

As will be appreciated by those skilled in the art, various means are available whereby such difference in absorbency can be realized. For example, such difference in absorbency can be realized through the use of materials having either or both different chemical formulation and physical characteristics, e.g., density. Thus, the broader practice of the invention is not limited by the particular technique by which such difference in absorbency is created or realized.

Suitable absorbent pad materials for use in the practice of the invention may include various absorbent materials and fluid conveyance barrier materials, such as are known in the art.

For example, selected absorbent materials for use in the practice of the invention can be fabricated or formed of various hydrophilic types of natural or synthetic fibers including cellulose fibers, surfactant-treated meltblown fibers, wood pulp fibers, regenerated cellulose, cotton fibers or a blend of other fibers.

Absorbent materials for use in the invention can include a material, generally known as coform, and described in U.S. Pat. No. 4,100,324, the disclosure of which is fully incorporated herein by reference. Coform is available from the Kimberly-Clark Corporation located in Neenah, Wis. and is generally a nonwoven material made up of an airform matrix of thermoplastic polymeric fibers and a multiplicity of individualized wood pulp fibers, and has a fabric-like finish. The thermoplastic fiber polymers generally have an average diameter of less than 10 microns with the individualized wood pulp fibers dispersed throughout the matrix and serving to space these microfibers from each other. Such material can be formed by initially utilizing the primary air stream with the meltblown microfibers and the secondary air stream containing wood pulp fibers and merging the two streams under turbulent conditions to form an integrated air stream along a forming surface.

In certain embodiments, the use of absorbent pad materials in the nature of surge materials may be desired. Various woven fabrics and nonwoven webs can be used to construct surge materials. For example, a surge material may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge material also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm.

Examples of particular surge materials may be found in U.S. Pat. No. 5,490,846 to Ellis et al. and in U.S. Pat. No. 5,364,382 to Latimer. Surge materials may be composed of a substantially hydrophobic material, and the hydrophobic material may optionally be treated with a surfactant or otherwise processed to impart a desired level of wettability and hydrophilicity.

Another possible suitable absorbent material is the material known as PRISM available from Kimberly-Clark Corporation. A description of PRISM is taught in U.S. Pat. No. 5,336,552 to Strack et al. and the disclosure of that patent is incorporated by reference herein in its entirety. PRISM is generally the nonwoven fabric and comprises extruded multicomponent polymeric strands including first and second polymeric components arranged in substantially distinctive zones across the cross-section of the multicomponent strands and extending continuously along the length of the multicomponent strands. Preferably, the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat. More specifically, the first polymeric component of the multicomponent strands is present in an amount of from about 20 to about 80 percent by weight of the strands and the second polymeric component is present in an amount from about 80 to about 20 percent by weight of the strands. Preferably, the first polymeric component of the multicomponent strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn and laid on a traveling forming surface.

The types of nonwoven materials that may be employed include powder-bonded-carded webs, infrared bonded carded webs, and through-air-bonded-carded webs. The infrared and through-air-bonded-carded webs can optionally include a mixture of different fibers, and the fiber lengths within a selected fabric web may be within the range of about 1.0 to 3.0 inch and an average bulk density of about 0.02 g/cc to about 0.12 g/cc.

Other suitable absorbent materials for use in the practice of the invention can include materials commonly referred to as superabsorbents. Known superabsorbent materials include AFA-1 30-53C by Dow Chemical, and W77553 and FAV880A which are commercially available from the Stockhausen Company of Greensboro, N.C. Stockhausen's W77553 is a bulk polymerized polyacrylate with a hydrophobic surface treatment. Stockhausen's FAV880A is a highly crosslinked surface superabsorbent. AFA 130-53C is a 850 to 1400 micron suspension polymerized polyacrylate material available from The Dow Chemical Company of Midland, Mich.

Hydrocolloidal materials, commonly referred to as superabsorbents, can be in the form of a hydrogel-forming polymer composition which is water-insoluble, slightly cross-linked, and partially neutralized. It can be prepared from an unsaturated polymerizable, acid group-containing monomers and cross-linked agents. Such superabsorbents are taught in U.S. Pat. No. 4,798,603 to Meyers et al., U.S. Reissue Patent 32,649 to Brandt et al. and U.S. Pat. No. 4,467,012 to Pedersen et al., as well as in published European Patent Application 0,339,461 to Kellenberger. The disclosures of these patents and the European Patent Application are incorporated by reference herein in their entirety.

Additionally, materials known as "slow rate" superabsorbents can also be used in the practice of the subject invention. By "slow rate" superabsorbent what is meant is a superabsorbent having an absorption time index (ATI) of at least 5 minutes and preferably more than 10 minutes. Adjusting the rate of absorbency of a superabsorbent may be achieved by modifications to the particle size, surface properties, and chemistry of the polymer. Such slow rate superabsorbents are described in greater detail in U.S. Pat. No. 5,843,063 to Anderson et al., the disclosure of which patent is incorporated herein its entirety.

Suitable absorbent materials for use in the practice of the invention may also take the form of absorbent foams such as open cell polyurethane foam, such as disclosed in U.S. Pat. No. 5,853,402 to Faulks et al., the disclosure of which patent is incorporated herein its entirety. Further, starch foams such as disclosed in U.S. Pat. No. 5,506,277 to Griesbach III, the disclosure of which patent is incorporated herein its entirety, may also be used.

The invention may also utilize, as suitable absorbent pad materials, corrugated nonwoven fabrics such as the high bulk corrugated nonwoven fabric disclosed in U.S. Pat. No. 3,668,054 to Stumpf, the disclosure of which patent is incorporated herein its entirety. As disclosed therein, such fabric generally comprises a corrugated web of initially aligned textile fibers implanted in a continuous thin film of a thermoplastic adhesive having an essentially constant thickness. The resulting web-adhesive material is then corrugated to provide the multitude of furrows and grooves, which are irregularly connected near their roots and along their respective sides.

As will be appreciated, appropriate materials for use in the practice of the invention can be variously suitably formed including being meltblown or airlaid or airformed. The term "meltblown fibers" generally refers to fibers formed by extruding a molten thermoplastic material through a plurality of fine, usually circular, die capillaries as molten threads or filaments and into converging high velocity gas (e.g., air) streams which attenuate the filaments of molten thermoplastic material to reduce their diameters. Thereafter, the meltblown fibers are typically carried by the high velocity gas stream and deposited on a collecting surface to form a web of randomly disbursed meltblown fibers. Meltblown fibers may be continuous or discontinuous and are generally tacky when deposited onto a collecting surface. Meltblown materials are described in greater detail in U.S. Pat. No. 5,656,361 to Vogt et al, the disclosure of which is fully incorporated herein by reference.

Further, absorbent pad materials of a construction which contain or include one or more of various additives such as coagulants, lysing agent or superabsorbents, for example, can also be used. Adjacent absorbent pad materials will preferably differ in one or more property or characteristic such as chemical composition or construction such as fiber orientation or thickness, for example. In accordance with one preferred embodiment of the invention, such adjacent absorbent pad materials advantageously preferably differ in a selected property or characteristic other than density and such as not easily obtainable with prior art techniques. In particular, the minimization or elimination of horizontal dependency by or between adjacent absorbent pad materials can result in the utilization of materials selected for special or particular properties or characteristic.

As will be appreciated by those skilled in the art and guided by the teachings herein provided, various suitable fluid conveyance barrier materials can be used in the practice of the invention. In particular, barrier members (also sometimes referred to as "flow regulating walls" or "fluid flow regulating walls") made of such barrier materials can take various forms and have a particular preselected permeability. Further, such barrier members may be incorporated in absorbent pad assemblies and absorbent articles in particular or specific arrangements such as to provide or result in particular or specific fluid flow control or management.

For example, one or more barrier members incorporated into an absorbent pad assembly and absorbent article in accordance with the invention may be semipermeable or impermeable to the fluid material to be controlled or regulated thereby, as may be specifically desired for or in a particular application or use. Alternatively or in addition, one or more barrier members incorporated into a particular absorbent pad assembly and absorbent article in accordance with the invention may be in the form of a fluid flow directional material.

Barrier members for use in the practice of the invention can be fabricated or formed of various suitable materials of preselected permeability, such as are known in the art. Suitable impermeable barrier members can, dependent on the particular application, coatings or films such as known in the art to prevent the transmission of fluid therethrough. For example, such an impermeable coating or film can be applied to a suitable substrate such as to form an impermeable barrier member. Further suitable impermeable barrier members can, dependent on the particular application, include impermeable backsheet materials, such as described above, or non-absorbent foams, such as a closed cell, crosslinked or a non-crosslinked polyolefin foam, including, for example, polypropylene or a polyethylene foam. Examples of commercially available foams contemplated for such use in the present invention include the trade name CA-30 foam manufactured by Sealed Air Corp. of Fair Lawn, N.J. and trade name AF-030 foam manufactured by Astro-Valcour, Inc. of Glens Falls, N.Y.

Semipermeable barrier members can be composed of such materials which permit or allow the transmission of only certain fluids therethrough. For example, the inclusion of such semipermeable barrier members can serve to filter or screen fluids be transmitted therethrough. Suitable semipermeable barrier members can, dependent on the particular application, include porous or perforated film or net-like materials such as described in U.S. Pat. No. 4,616,644 to Saferstein et al. and U.S. Pat. No. 5,643,240 to Jackson et al., the disclosures of which are incorporated by reference herein in their entirety. For example, U.S. Pat. No. 4,616,644 discloses a series of light weight, nonwoven fabrics made from high-density polyethylene or polypropylene through a process of extrusion, embossing and orientation and referred to as Delnet film, available from Hercules Inc. and U.S. Pat. No. 5,643,240 discloses a suitable apertured film referred to as AET polyethylene CKX 215 film made by Applied Extrusion Technology of Middleton, Del.

Directional or flow directional barrier members can act like check valves to allow fluid to pass therethrough primarily in one direction. For example, an apertured film such as known for use as top or body-side surfaces in such absorbent articles can be used for such purposes.

Thus, barrier members used in the practice of the invention can be fabricated of various films, foams and the like. Further, in accordance with certain preferred embodiments of the invention, one or more of the barrier members may be in the form of such a film, foam or the like and which, is dissolvable after fluid contact such as to provide or result in a time release effect.

Moreover, it is to be understood that the broader practice of the invention is not necessarily limited to specific or particular absorbent pad materials and that other absorbent pad materials such as are known to those skilled in the art can, if desired, be used. For example, a wide assortment of materials have been designed and developed to better handle or address the various conditions to which such products may be required to perform.

Returning to FIG. 1, while the mandrel 40 has been illustrated as having a generally circular cross section, other suitable shapes or forms of mandrel can, if desired, be used. For example, mandrels having an oval or rectangular cross section can be use, if desired.

Figure 2:
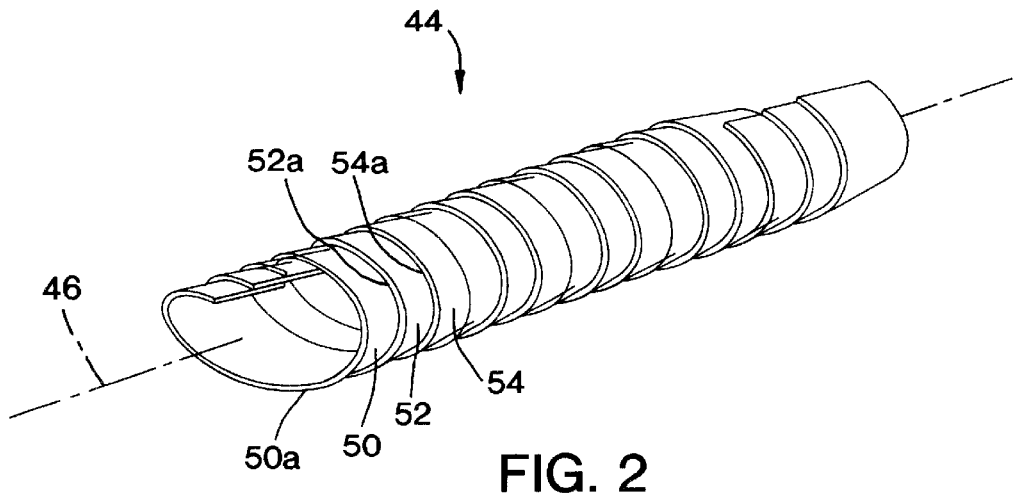
FIG. 2 is a simplified fragmentary perspective view of an absorbent pad assembly in accordance with another preferred embodiment of the invention.
Figure 3:
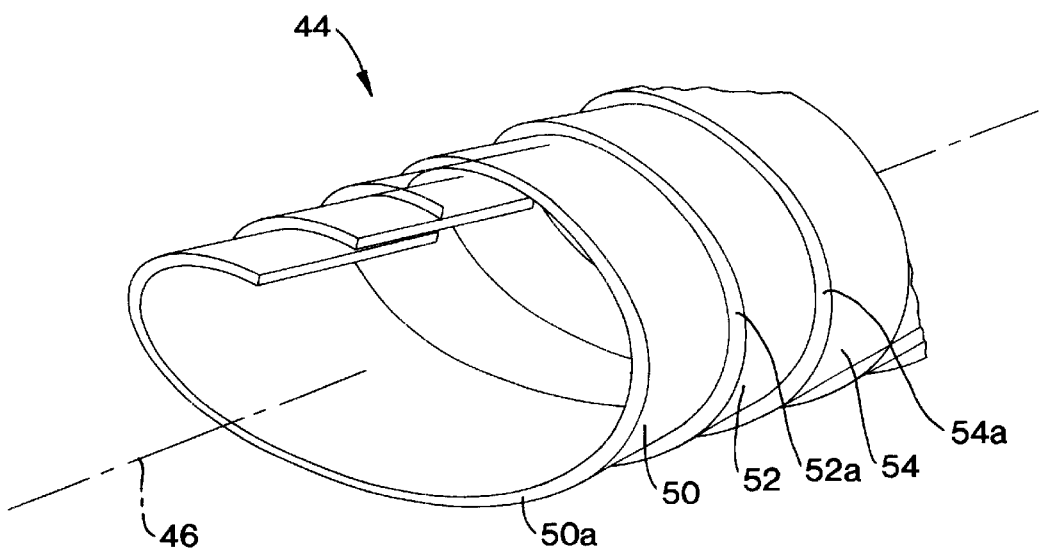
FIG. 3 is an enlargement of a fragmentary end portion of the absorbent pad assembly shown in FIG. 2.
Figure 4:
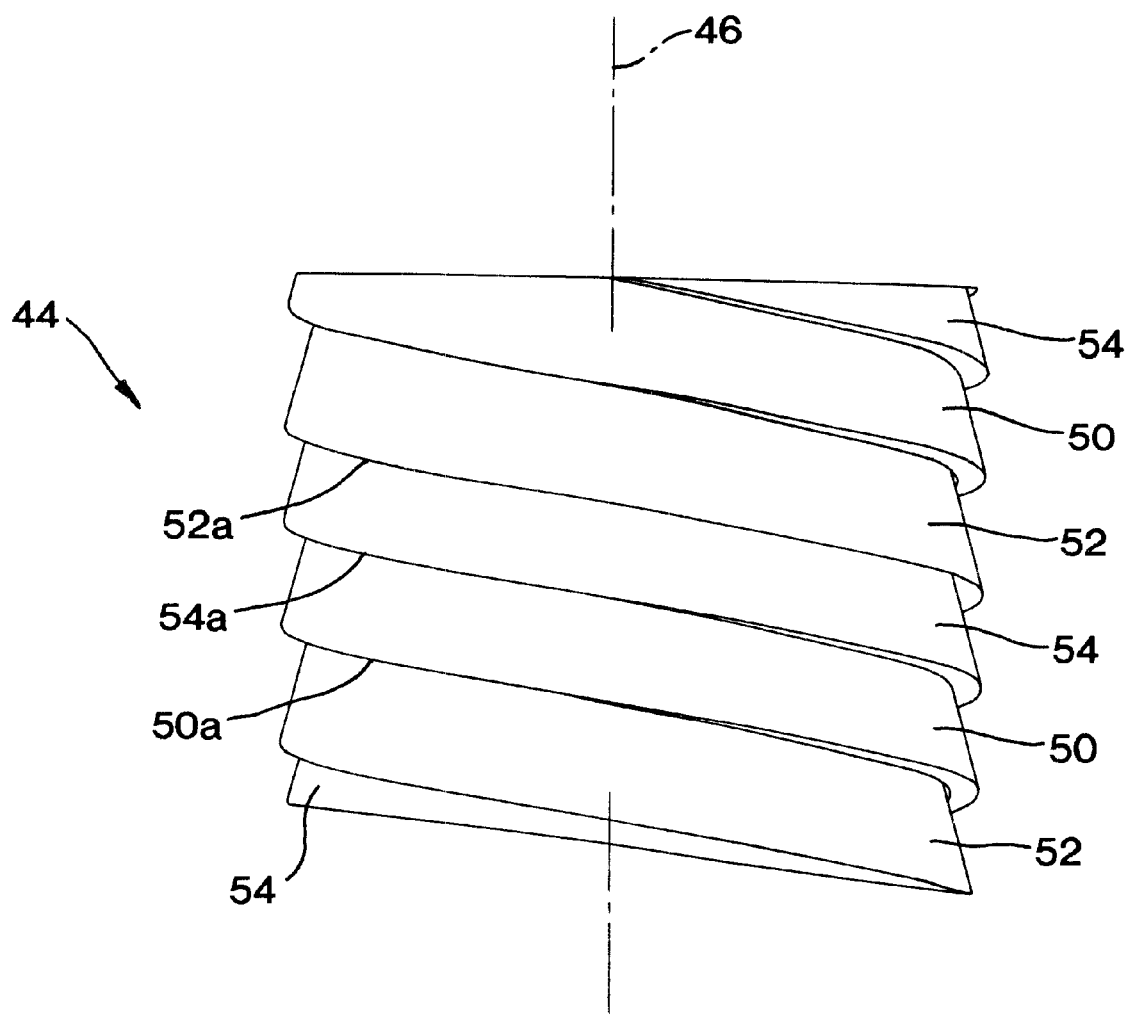
FIG. 4 is a fragmentary side view of an absorbent pad assembly in accordance with one embodiment of the invention.

Further, while the absorbent pad assembly 30 shown in FIG. 1 is illustrated in association with the mandrel 40, it will be appreciated that final absorbent pad assembly products in accordance with the invention may be free of such or similar mandrels. Thus, FIGS. 2–4 illustrate a similar absorbent pad assembly 44, having a longitudinal axis 46, and which absorbent pad assembly is free of such a mandrel.

The absorbent pad assembly 44, similar to the absorbent pad assembly 30 described above, includes adjacent windings of three webs of absorbent pad material, individually designated 50, 52 and 54. Each of the absorbent pad material webs 50, 52 and 54, respectively, includes an edge surface, individually designated 50a, 52a and 54a, respectively. As shown, each absorbent pad material web 50, 52 and 54 is wound about the longitudinal axis 46, such that edge surfaces 50a, 52a and 54a, respectively, are angularly orientated relative to the longitudinal axis 46, perhaps as best seen by reference to FIG. 4.

Figure 5:
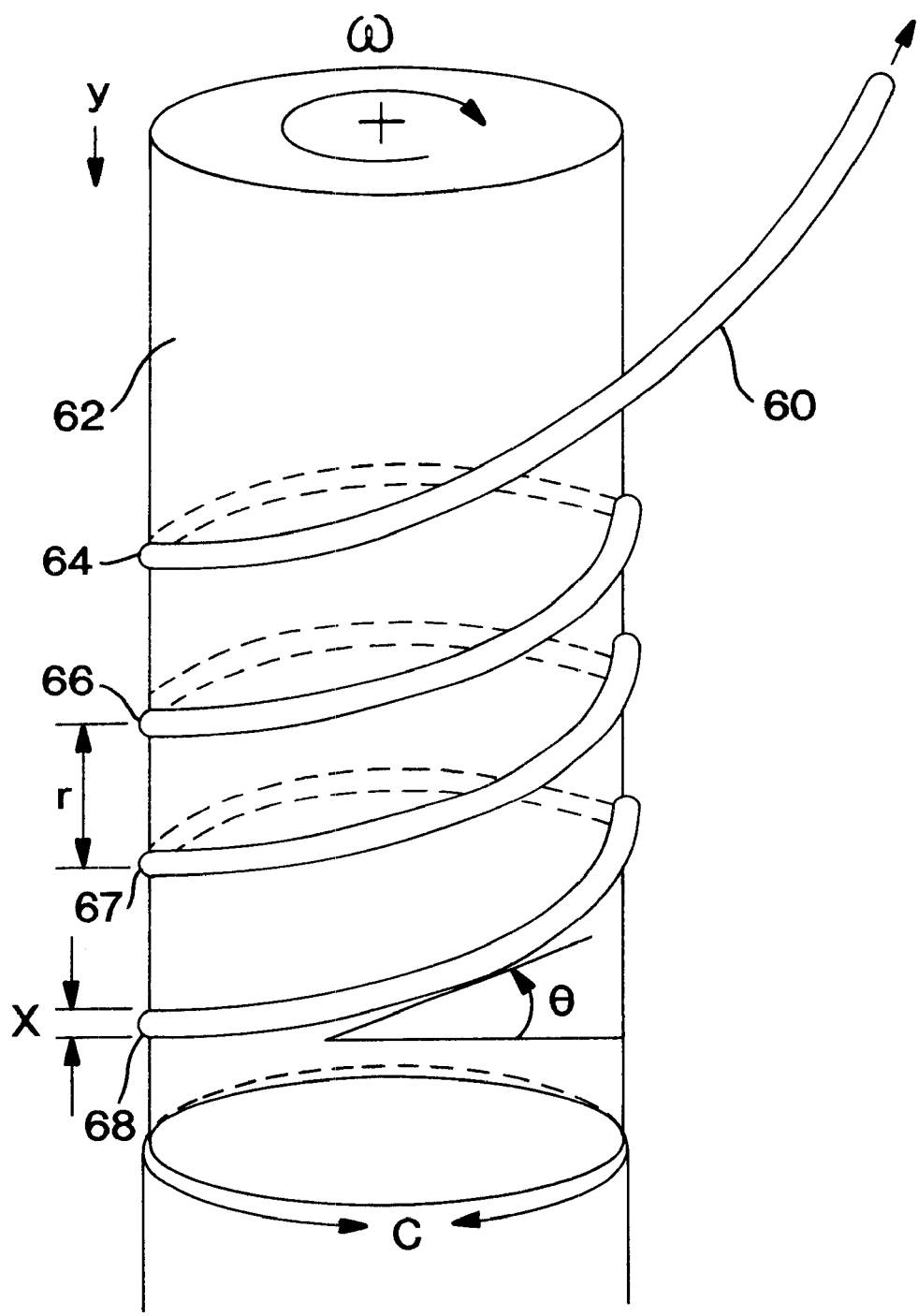
FIG. 5 is a perspective schematic illustrating the making of absorbent pad assembly in accordance with one embodiment of the invention.

FIG. 5 illustrates the winding of an absorbent pad material web 60 about a mandrel or shaft 62, in accordance with one embodiment of the invention. In particular, the absorbent pad material web 60 has a width designated "x" and the mandrel or shaft 62 has a circumference designated "c." Further, the absorbent pad material web 60 is applied to the mandrel 62 at a web angle designated "θ," an axial velocity designated "y" and an angular velocity designated "ω."

The absorbent pad material web 60, as shown in FIG. 5, is desirably wound in a helical fashion and includes a plurality of rungs, individually designated by the reference numerals 64, 66, 67, and 68. As shown, each such rung is desirably axially displaced from the next adjacent rung by a preselected spacing designated "r." Such rung spacing, can be the same (e.g., uniform) or different (e.g., such as varying in a selected pattern) along the longitudinal axis being formed thereby.

Those skilled in the art and guided by the teachings herein provided will recognize and appreciate that through the proper selection of particular absorbent materials and particular formation parameters including: absorbent material web widths, shaft circumference, web angles, axial velocities, angular velocities, rung spacing, specifically desired absorbent structures may be provided.

In particular, it is to be appreciated that the absorbent pad material web 60 can constitute one or more absorbent material webs being wrapped simultaneously. Alternatively, or in addition, individual absorbent material webs or combinations can be placed in register and wrapped at a desired spacing. Further, particular individual absorbent material webs or combinations can be wrapped at the same or different web angles, axial velocities and angular velocities, as may be desired, such as to provide an absorbent product having particular absorbent qualities or characteristics. In general, the extent of overlap or spacing of adjacent absorbent material webs will be dependent on the particular web widths, shaft circumference, web angles, axial velocities and angular velocities.

The invention has been described above with reference to absorbent pad assemblies having a central mandrel or shaft, e.g., the absorbent pad assembly 30 having the mandrel 40, as well as absorbent pad assemblies free of such mandrel or shaft, e.g., the absorbent pad assembly 44. Thus, it is to be understood that the invention can, as desired, be practiced via embodiments wherein such central shaft or mandrel is in the form of a temporary processing aid, such as a machine part, or embodiments wherein the central shaft or mandrel is or becomes a permanent or component part of the absorbent pad assembly or associated absorbent article or product, such as where the shaft or mandrel is formed or fabricated of a suitable absorbent material or other suitable absorbent product material.

FIGS. 6–9 are simplified side view schematics illustrating the positioning of sections of different absorbent pad materials in different absorbent pad assemblies, in accordance with alternative embodiments of the invention and absorbent pad assemblies are individually designated by the reference numerals 70, 72, 74, and 76, respectively.

The absorbent pad assembly 70, shown in FIG. 6, is shown in relation to a central mandrel or shaft 80 and includes adjacent windings of three webs of absorbent pad material, individually designated 82, 84 and 86. In this particular embodiment, the sections of the individual webs or plies 82, 84, and 86 are shown spaced apart by a selected web spacing designated "w" and such as discussed above.

The absorbent pad assembly 72, shown in FIG. 7, includes adjacent windings of three webs of absorbent pad material, individually designated 92, 94 and 96, wherein the sections of the individual webs or plies are in abutting relationship such that there is neither a gap (as shown in the absorbent pad assembly 70 shown in FIG. 6) nor an overlap (as discussed below) of such adjacent absorbent material webs.

The absorbent pad assembly 74, shown in FIG. 8 includes adjacent windings of three webs of absorbent pad material, individually designated 102, 104 and 106, wherein the sections of the individual webs or plies are in overlapping relationship. In particular, each of the individual webs or plies 102, 104 and 106 overlap with one or more of the other of these individual webs or plies. More specifically, webs 102 and 106 each have an overlapping portion with web 104, while web 104 includes overlapping portions with each of webs 102 and 106. As will be appreciated, such overlap can be achieved by various means including, for example, by simply altering the relative placement of the individual absorbent pad material webs or by increasing the width of particular individual absorbent pad material webs.

The absorbent pad assembly 76, shown in FIG. 9, includes adjacent windings of three webs of absorbent pad material, individually designated 112, 114 and 116 wherein the sections of the individual webs or plies are again in overlapping relationship. In the absorbent pad assembly 76, however, the overlap is multiple in nature as, for example, an overlap is formed by each of the three webs 112, 114 and 116.

Figure 12:
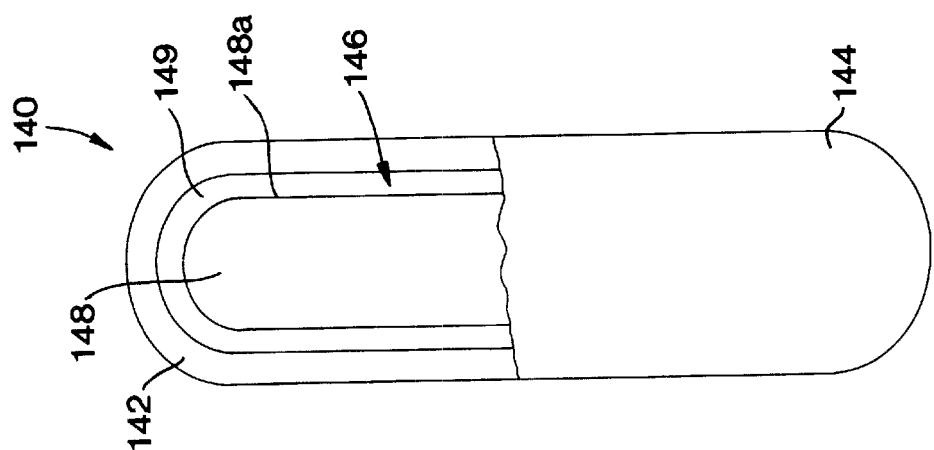
FIGS. 10–12 are simplified fragmentary top view schematics of absorbent articles in accordance with alternative embodiments of the invention.
Figure 11:
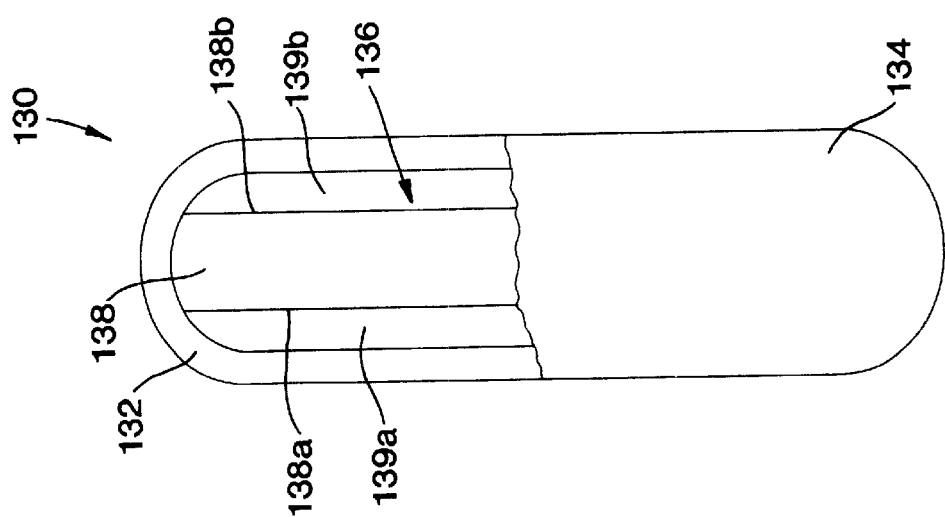
Figure 10:
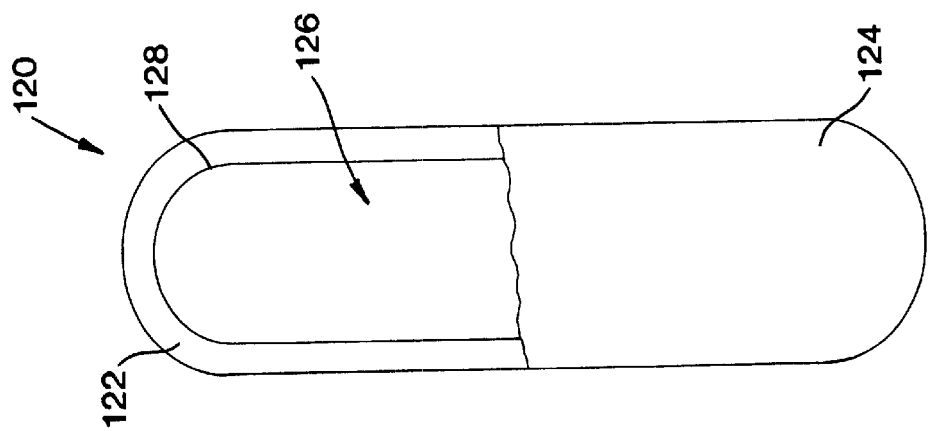

FIGS. 10–12 are simplified fragmentary top view schematics of absorbent articles, such as in the form of sanitary napkins, each containing or including an absorbent pad assembly in accordance with certain preferred alternative embodiments of the invention.

FIG. 10 illustrates a sanitary napkin 120 which includes a generally liquid impervious backsheet or baffle 122 on the garment-facing side of the article, a generally liquid previous topsheet or cover 124 on an opposing body-facing side of the article, and an absorbent core 126, disposed and enclosed therebetween. The absorbent core 126 is generally in the form of an absorbent pad assembly 128, such as described above, and which pad assembly is centrally positioned or placed in the absorbent article 120 between the backsheet 122 and the topsheet 124.

Such absorbent article topsheet or covers are generally designed to contact the body of the user and generally forms the contact surface of the respective absorbent article. In practice, topsheet can be constructed of a woven or nonwoven material, from synthetic or natural materials and desirably should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely perforated film webs and net material also work well. Further, suitable topsheet may also be constructed of a thermoplastic film which contains apertures and is flanked on one or both sides by a nonwoven material. Such an embodiment may desirably present a relatively soft feel against a user's thigh while allowing the rapid passage therethrough of body fluid.

The backsheets or baffles of such absorbent articles are generally liquid impermeable and designed to face the inner face, e.g., the crotch portion, of an undergarment (not shown). Such backsheets may desirably be designed to permit the passage of air or vapor out of the absorbent article while preventing or blocking the passage of fluids therethrough. As will be appreciated, such backsheets can be made of any suitable material capable of providing or having the above-identified properties or characteristics. For example, suitable materials may include a microembossed polymeric film such as of polyethylene or polypropylene.

As will be appreciated, the topsheet and the backsheet of a respective absorbent article can be placed coextensive, in face-to-face contact around or about an associated absorbent core, with the peripheries of the topsheet and the backsheet desirably joined or sealed together by use of an adhesive, by heat sealing ultrasonics or other suitably selected techniques such as are known to those skilled in the art.

It will be appreciated that absorbent articles such as feminine care products such as sanitary napkins may typically include additional standard or usual features such as relating to the positioning or placement of the article when in use. For example, certain sanitary napkin designs incorporate side flaps, sometimes referred to as "wings," such as can be helpful in preventing fluid flow from the sides of the napkin. Another example of such a feature is the inclusion or presence of an adhesive at or about the garment facing region face of the backsheet. Such adhesive surface of the article can be covered by a release paper or the like, as is known in the art, prior to use such as when in a packaged state. As such features are standard or common, are well known to those skilled in that art and form no part of the broader invention, they will not be shown or described in great detail herein.

FIG. 11 illustrates a sanitary napkin 130 which includes a backsheet 132, a topsheet 134 and an absorbent core 136. The absorbent core 136 includes a centrally positioned or placed absorbent pad assembly 138, similar to that described above. In addition, the absorbent core 136 also includes additional absorbent elements 139*a* and 139*b* at the first and second longitudinal sides 138*a* and 138*b*, respectively, of the absorbent pad assembly 138. As will be appreciated, the additional absorbent elements 139*a* and 139*b* can be continuous or noncontinuous, as may be desired for specific applications.

FIG. 12 illustrates a sanitary napkin 140 which includes a backsheet 142, a topsheet 144 and an absorbent core 146. The absorbent core 146 includes a centrally positioned or placed absorbent pad assembly 148, similar to that described above. In addition, the absorbent core 148 includes an absorbent element 149 at the perimeter 148*a* of the absorbent pad assembly 148.

Figure 13:
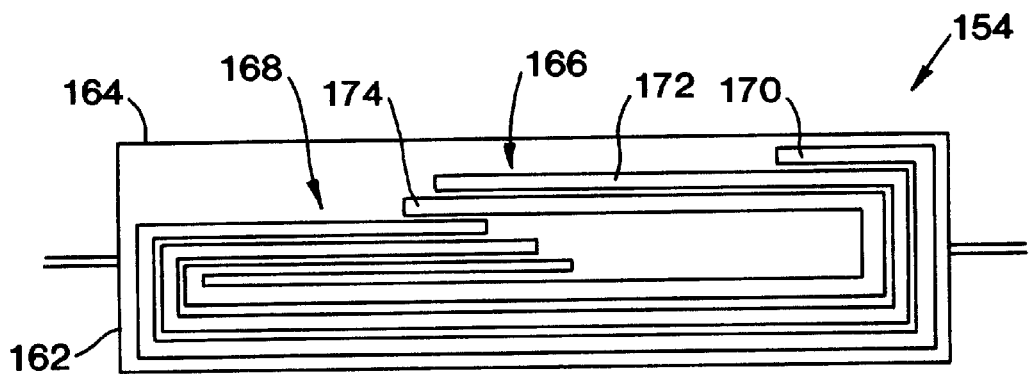
FIGS. 13–15 are simplified sectional side view schematics of absorbent articles in accordance with alternative embodiments of the invention.
Figure 14:
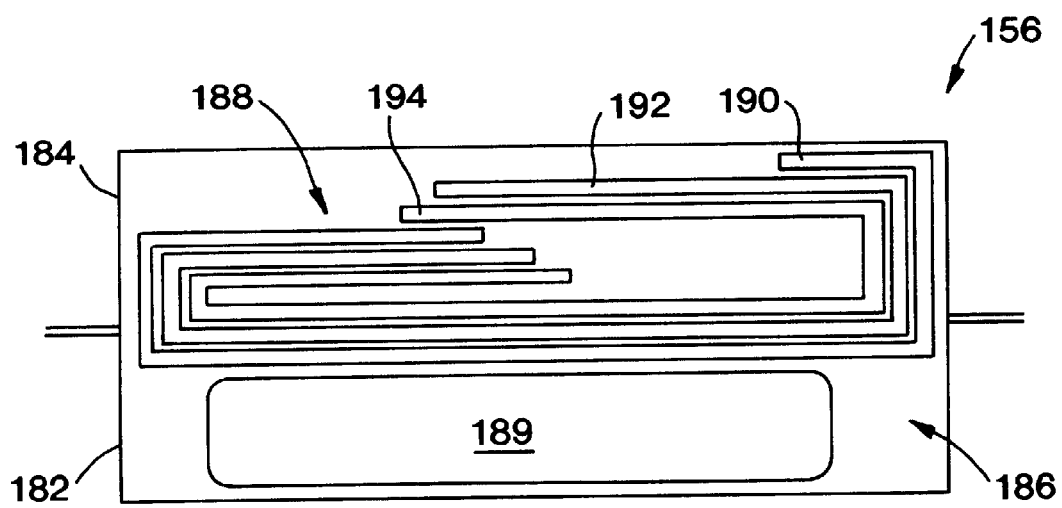
Figure 15:
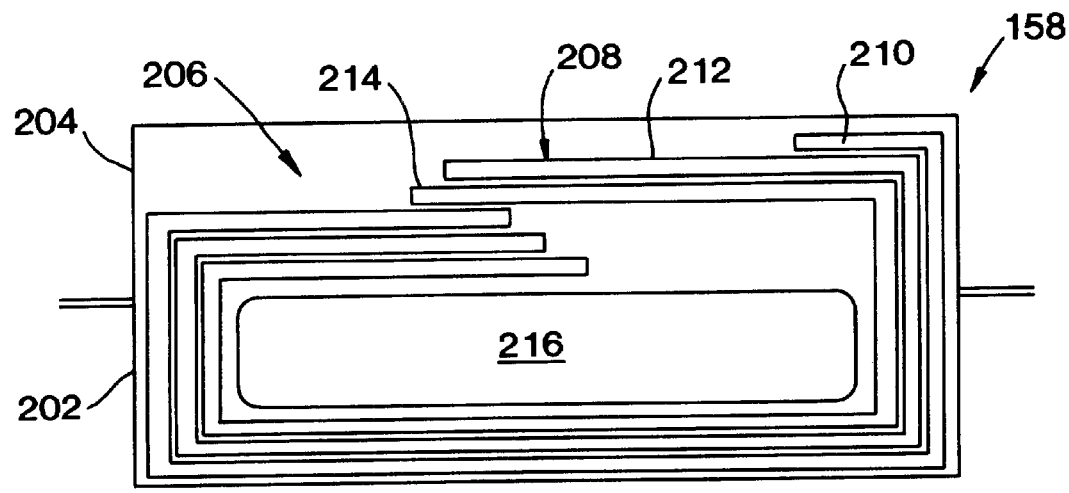

FIGS. 13–15 are simplified schematic sectional views of absorbent articles, e.g., sanitary napkins, in accordance with alternative embodiments of the invention and individually designated by the reference numerals 154, 156 and 158, respectively.

FIG. 13 illustrates the sanitary napkin 154 which includes a backsheet 162, a topsheet 164, such as described above, and an absorbent core 166. The absorbent core 166 includes an absorbent pad assembly 168, in accordance with the invention and such as described above. More specifically, the absorbent pad assembly 168 is generally composed of a plurality of adjacent windings of webs of absorbent pad material, individually designated 170, 172 and 174.

As shown, the absorbent pad assembly 168 is free of a central mandrel or shaft and the absorbent pad assembly has been flattened along such longitudinal axis, such as to result in a shape or form suitable for the particular intended use of the absorbent article, e.g., as a feminine care sanitary napkin.

FIG. 14 illustrates the sanitary napkin 156 which, similar to the sanitary napkin 150 described above, includes a corresponding backsheet 182, a topsheet 184, and an absorbent core 186. The absorbent core 186 includes an absorbent pad assembly 188, in accordance with the invention and such as described above. More specifically, the absorbent pad assembly 188 is generally composed of a plurality of adjacent windings or rungs of webs of absorbent pad material, individually designated 190, 192 and 194. As described above, such an absorbent pad assembly desirably can serve to provide an outer surface such as composed of various specifically selected materials and such as may provide improved performance characteristics in particular product applications.

The absorbent core 186 also includes a structural element, designated by the reference numeral 189. Such a structural element may be disposed adjacent the absorbent pad assembly in underlying or overlying relation (as shown), or internally adjacently disposed therewithin, as described below with reference to FIG. 15. Further, while the structural element 189 is illustrated in FIG. 14 as being narrower than the associated absorbent pad assembly 188, the broader practice of the invention is not necessarily so limited. For example, structural elements having a width which is the same or greater than the associated absorbent pad assembly can, if desired, be used therewith.

Suitable structural elements for use in the practice of the invention can be variously constructed or formed as will be appreciated by those skilled in the art. Possible materials for use as such structural elements include absorbent fluff material, as is known for use in various absorbent articles, or other absorbent materials such as described above. Alternatively or in addition, the structural element may be formed of or include a non-absorbent material, such as a non-absorbent resiliency-member material such as a non-absorbent flexible foam or the like such as may be added or included to provide improved resiliency, for example.

FIG. 15 illustrates the sanitary napkin 158 which, similar to the sanitary napkins 154 and 156 described above, includes a corresponding backsheet 202, a topsheet 204 and an absorbent core 206. The absorbent core 206, similar to the absorbent cores 166 and 186 described above includes a corresponding absorbent pad assembly 208 such as generally composed of a plurality of adjacent windings of webs of absorbent pad material, individually designated 210, 212 and 214.

The absorbent core 206, however, also includes a structural element 216 centrally located within the adjacent absorbent pad assembly 208. Such a structural element 216 may, if desired, be in the form of the mandrel or shaft such as may have been used in the formation of the adjacent absorbent pad material web windings. Alternatively or in addition, such structural element may take a form such as described above and simply be inserted, placed or positioned within an absorbent pad assembly in accordance with the invention, such as formed as described above or otherwise formed.

While the invention has been described above relative to absorbent articles wherein the absorbent core contains a single absorbent pad assembly in accordance with the invention, it is to be understood that the broader practice of the invention is not necessarily so limited. For example, as will be appreciated by those skilled in the art, the invention can, if desired, be practiced with absorbent articles containing two or other selected multiple of such absorbent pad assemblies. Further, such absorbent articles may contain such two or more absorbent pad assemblies in spaced apart, overlying, partially overlapping or other selected relationship, as may be desired for a particular application.

Thus, the invention provides absorbent pad assemblies and absorbent articles which permit the more complete or full utilization of the absorbent capacity thereof as may be desired. The invention also generally provides absorbent pad assemblies and absorbent articles which can respond to the possibly wide range of operating and performance conditions to which such assemblies and articles can be exposed in an as effective and efficient a manner as may be desired.

The invention further provides for the simplified manufacture and production of such absorbent pad assemblies and associated absorbent articles.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. A method for forming an absorbent article having an absorbent pad assembly with an outer fluid-contacting surface including discrete portions of different absorbency comprising:

helically winding at least first and second absorbent pad materials adjacently about a shaft member whereby at least a portion of each of the first and second absorbent pad materials includes an outer surface exposed portion.

2. The method of claim 1 wherein the first absorbent pad material comprises a first absorbent material having a first preselected absorbency.

3. The method of claim 2 wherein the second absorbent pad material comprises a second absorbent material having a second preselected absorbency wherein the second preselected absorbency is different from the first preselected absorbency.

4. The method of claim 1 wherein the first absorbent pad material comprises a fluid conveyance barrier member of preselected permeability.

5. The method of claim 4 wherein the fluid conveyance barrier member comprises an impermeable material.

6. The method of claim 4 wherein the fluid conveyance barrier member comprises a flow directional material.

7. The method of claim 4 wherein the fluid conveyance barrier member comprises a semipermeable material.

8. A method for forming an absorbent article having an absorbent pad assembly with an outer fluid-contacting surface including discrete portions of different absorbency comprising:

helically winding at least first and second absorbent pad materials adjacently about a shaft member whereby at least a portion of each of the first and second absorbent pad materials includes an outer surface exposed portion, wherein the shaft member at least in part forms a component part of the absorbent article.

9. The method of claim 1 wherein the first and second adjacent absorbent web materials have a preselected amount of overlap.

10. The method of claim 1 wherein the first and second adjacent absorbent pad materials have a preselected spacing between adjacent helical rungs.

11. The method of claim 1 additionally comprising a third absorbent pad material helically wound adjacent at least the second absorbent pad material.

12. The method of claim 1 additionally comprising:

disposing an absorbent core structural element adjacent the absorbent pad assembly.

13. The method of claim 12 wherein the absorbent core structural element is disposed in underlying relation with the absorbent pad assembly.

14. The method of claim 12 wherein the absorbent core structural element is disposed in overlying relation with the absorbent pad assembly.

15. The method of claim 12 wherein the absorbent core structural element is disposed internally adjacent within the absorbent pad assembly.

16. The method of claim 12 wherein the absorbent core structural element comprises an absorbent material of preselected absorbency.

17. The method of claim 12 wherein the absorbent core structural element comprises a non-absorbent material.

18. The method of claim 12 wherein the absorbent core structural element comprises a non-absorbent resiliency-member material.

19. A method for forming an absorbent article having an absorbent pad assembly with an outer fluid-contacting surface including discrete portions of different absorbency comprising:

helically winding at least first and second absorbent pad materials adjacently about a shaft member whereby at least a portion of each of the first and second absorbent pad materials includes an outer surface exposed portion, wherein the absorbent pad assembly has a longitudinal axis and wherein the method additionally comprises the step of flattening the absorbent pad assembly along the longitudinal axis thereof.

20. A method for forming an absorbent article having at least a first and a second absorbent pad assembly, each of the first and second absorbent pad assemblies having an outer fluid-contacting surface including discrete portions of different absorbency comprising:

helically winding at least first and second absorbent pad materials adjacently about a shaft member whereby at least a portion of each of the first and second absorbent pad materials includes an outer surface exposed portion.

21. The method of claim 20 wherein the first and second absorbent pad assemblies are in spaced apart relationship.

22. The method of claim 20 wherein the first and second absorbent pad assemblies are in overlying relationship.

23. The method of claim 20 wherein the first and second absorbent pad assemblies are in partially overlapping relationship.

24. A method for forming an absorbent article having an absorbent pad assembly with a longitudinal axis and an outer fluid-contacting surface including discrete portions of different absorbency comprising:

helically winding at least first, second and third absorbent pad materials adjacently about a shaft member whereby at least a portion of each of the first, second and third absorbent pad materials includes an outer surface exposed portion;

flattening the absorbent pad assembly along the longitudinal axis thereof; and placing an absorbent core including the flattened absorbent pad assembly between a backsheet and a topsheet.

25. The method of claim 24 wherein the absorbent article is in the form of a sanitary napkin.

26. The method of claim 19 wherein the first absorbent pad material comprises a first absorbent material having a first preselected absorbency.

27. The method of claim 26 wherein the second absorbent pad material comprises a second absorbent material having a second preselected absorbency wherein the second preselected absorbency is different from the first preselected absorbency.

28. The method of claim 19 wherein the first absorbent pad material comprises a fluid conveyance barrier member of preselected permeability.

29. The method of claim 28 wherein the fluid conveyance barrier member comprises an impermeable material.

30. The method of claim 28 wherein the fluid conveyance barrier member comprises a flow directional material.

31. The method of claim 28 wherein the fluid conveyance barrier member comprises a semipermeable material.

32. The method of claim 19 wherein the first and second adjacent absorbent web materials have a preselected amount of overlap.

33. The method of claim 19 wherein the first and second adjacent absorbent pad materials have a preselected spacing between adjacent helical rungs.

34. The method of claim 19 additionally comprising a third absorbent pad material helically wound adjacent at least the second absorbent pad material.

35. The method of claim 19 additionally comprising:

disposing an absorbent core structural element adjacent the flattened absorbent pad assembly.

36. The method of claim 35 wherein the absorbent core structural element is disposed in underlying relation with the flattened absorbent pad assembly.

37. The method of claim 35 wherein the absorbent core structural element is disposed in overlying relation with the flattened absorbent pad assembly.

38. The method of claim 35 wherein the absorbent core structural element comprises an absorbent material of preselected absorbency.

39. The method of claim 35 wherein the absorbent core structural element comprises a non-absorbent material.

40. The method of claim 35 wherein the absorbent core structural element comprises a non-absorbent resiliency-member material.

* * * * *